(12) United States Patent
Moore

(10) Patent No.: US 8,162,820 B2
(45) Date of Patent: *Apr. 24, 2012

(54) STEREOVIDEOSCOPE AND METHOD OF USING THE SAME

(76) Inventor: Kent Moore, Charlotte, NC (US)

( * ) Notice: Subject to any disclaimer, the term of this patent is extended or adjusted under 35 U.S.C. 154(b) by 770 days.

This patent is subject to a terminal disclaimer.

(21) Appl. No.: 12/300,923

(22) PCT Filed: May 16, 2007

(86) PCT No.: PCT/US2007/069025
§ 371 (c)(1),
(2), (4) Date: Nov. 14, 2008

(87) PCT Pub. No.: WO2007/137059
PCT Pub. Date: Nov. 29, 2007

(65) Prior Publication Data
US 2009/0198100 A1    Aug. 6, 2009

Related U.S. Application Data

(60) Provisional application No. 60/747,468, filed on May 17, 2006.

(51) Int. Cl.
*A61B 1/00* (2006.01)
*A61B 5/08* (2006.01)

(52) U.S. Cl. ......... 600/111; 600/166; 600/118; 600/529

(58) Field of Classification Search .................. 600/107, 600/111, 166, 118, 538, 532, 539; 348/45, 348/65, 74

See application file for complete search history.

(56) References Cited

U.S. PATENT DOCUMENTS

| 4,651,201 | A | * | 3/1987 | Schoolman | 348/45 |
| 4,746,203 | A | * | 5/1988 | Nishioka et al. | 359/834 |
| 4,935,810 | A | * | 6/1990 | Nonami et al. | 348/45 |
| 5,474,519 | A |   | 12/1995 | Bloomer | |
| 5,751,341 | A |   | 5/1998 | Chaleki et al. | |
| 5,882,314 | A |   | 3/1999 | Fredberg et al. | |

(Continued)

FOREIGN PATENT DOCUMENTS

WO    WO-2005/048827 A1    6/2005

(Continued)

OTHER PUBLICATIONS

International Search Report and Written Opinion for International Appl. No. PCT/US2007/069025, mailed Feb. 1, 2008.

(Continued)

*Primary Examiner* — John P Leubecker
(74) *Attorney, Agent, or Firm* — Alston & Bird LLP

(57) ABSTRACT

A system and method for acquiring measurements of a portion of a patient's anatomy are provided. For example, the system includes a stereovideoscope including a scope coupled to a flexible tubing and configured to be positioned within the patient's body. The scope includes a plurality of stereoscopic lenses configured to capture data indicative of the portion of the patient's anatomy, and the flexible tubing includes a biocompatible material. In addition, the system includes a processing element that is in communication with the stereovideoscope and that is configured to generate an image based on the captured data in order to acquire at least one geometrical measurement indicative of the portion of the patient's upper airway and to determine a probabilty of the patient's response to a tongue-base treatment based on the at least one geometrical meaurement.

19 Claims, 5 Drawing Sheets

U.S. PATENT DOCUMENTS

| | | | |
|---|---|---|---|
| 5,919,128 A | 7/1999 | Fitch | |
| 5,989,185 A * | 11/1999 | Miyazaki | 600/175 |
| 6,083,173 A * | 7/2000 | Grant et al. | 600/529 |
| 6,190,328 B1 | 2/2001 | Ruton et al. | |
| 6,342,039 B1 | 1/2002 | Lynn et al. | |
| 6,409,676 B2 | 6/2002 | Ruton et al. | |
| 6,440,083 B1 * | 8/2002 | Fredberg et al. | 600/533 |
| 6,801,325 B2 | 10/2004 | Farr et al. | |
| 6,817,975 B1 | 11/2004 | Farr et al. | |
| 6,914,623 B2 * | 7/2005 | Ogawa | 348/45 |
| 6,988,994 B2 | 1/2006 | Rapoport et al. | |
| 7,048,685 B2 * | 5/2006 | Sakiyama | 600/175 |
| 7,186,221 B2 | 3/2007 | Rapoport et al. | |
| 7,697,968 B2 | 4/2010 | Moore | |
| 2001/0000346 A1 | 4/2001 | Ruton et al. | |
| 2002/0137986 A1 | 9/2002 | Ogawa | |
| 2003/0060679 A1 * | 3/2003 | Murata et al. | 600/111 |
| 2005/0027207 A1 | 2/2005 | Westbrook et al. | |
| 2005/0115561 A1 | 6/2005 | Stahmann et al. | |
| 2006/0241708 A1 * | 10/2006 | Boute | 607/17 |

FOREIGN PATENT DOCUMENTS

| | | |
|---|---|---|
| WO | WO-2006/007865 A1 | 1/2006 |

OTHER PUBLICATIONS

Yueha Liu, DDS, PhD, et al.; *Cephalometric and physiologic predictors of the efficacy of an adjustable oral appliance for treating obstructive sleep apnea*; American Journal of Orthodontics and Dentofacial Orthopedics; Dec. 2001; pp. 639-647.

G. Mayer and K. Maier-Ewert; *Cephalometric predictors for orthopaedic mandibular advancement in obstructive sleep apnoea*; European Journal of Orthodontics; 17 (1995); pp. 35-43.

Ama Johal, Joanna M. Battagel and Bhik T. Kotecha; *Sleep Nasendoscopy: A diagnostic tool for predicting treatment success with mandibular advancement splints in obstructive sleep apnoea*; European Journal of Orthodontics; 27 (2005); pp. 607-614.

J M Battagel, PhD, Fds, Rcs, et al; Sleep nasendoscopy as a predictor of treatment success in snorers using mandibular advancement splints; the Journal of Larngology & Otology; Feb. 2005; vol. 119; pgs. 106-112.

Clete A. Kushida, MD, PhD., et al.; *Practice Parameters for the Treatment of Snoring and Obstructive Sleep Apnea with Oral Appliances*: An Update for 2005; An American Academy of Sleep Medicine Report; pp. 1-9 (2006).

Kathleen A. Ferguson, MD, et al.; *Oral Appliances for Snoring and Obstructive Sleep Apnea: A Review*; pp. 1-77 (2006).

*Iplex Manager, Olympus*; 3 pages, available at <http://iplex.olympusindustrial.com/iplex/eng/product/features/iplex_manager.html>; downloaded Feb. 20, 2006.

*Super Stereo Management; Olympus*; 4 pages, available at <http://iplex.olympusindustrial.com/iplex/eng/product/features/super_stereo.html>; downloaded Feb. 20, 2006.

*Versatile Performance; Olympus*; 5 pages, available at <http://iplex.olympusindustrial.com/iplex/eng/product/features/versatile.html>; downloaded Feb. 20, 2006.

*Flexible Videoscope; Olympus Industrial Home*; 5 pages, available at <http://olympus.com.sg/ind_endoscopy/product/videoscope/video.html>; downloaded Feb. 20, 2006.

Fleury et al., "Mandibular Advancement Titration for Obstructive Sleep Apnea: Optimization of the Procedure by Combining Clinical and Oximetric Parameters," *CHEST*, 2004; 125; pp. 1761-1767.

Battagel et al., "The Role of Lateral Cephalometric Radiography and Fluoroscopy in Assessing Mandibular Advancement in Sleep-Related Disorders," *European Journal of Orthodontics*, 1998, vol. 20, pp. 121-132.

"Remote Visual Inspection Products," 2 pages, available at <http://www.geinspectiontechnologies.com/en/products/rvi/index.html>; downloaded May 11, 2006.

"Video Borescopes," 2 pages, available at <http://www.geinspectiontechnologies.com/en/products/rvi/vp/index.html>; downloaded May 11, 2006.

"Flexible Fiberscopes," 2 pages, available at <http://www.geinspectiontechnologies.com/en/products/rvi/fiberscopes/index.html>; downloaded May 11, 2006.

"Olympus Industrial—Videoscopes," 20 pages, available at <http://www.olympusindustrial.com>; downloaded May 11, 2006.

"Olympus Anesthesiology Products—Anesthesiologists—Fiberscopes—Bronchoscopes," 20 pages, available at <http://www.olympusamerica.com/msg_section/msg_anesth.asp>; downloaded May 11, 2006.

Kasey K.L. et al.: "Obstructive Sleep Apnea and Maxillomandibular Advancement: An Assessment of Airway Changes Using Radiographic and Nasopharyngoscopic Examinations"; Journal of Oral Maxillofacial Surgery; vol. 60 (5); May 2002; pp. 526-530; XP008109513.

* cited by examiner

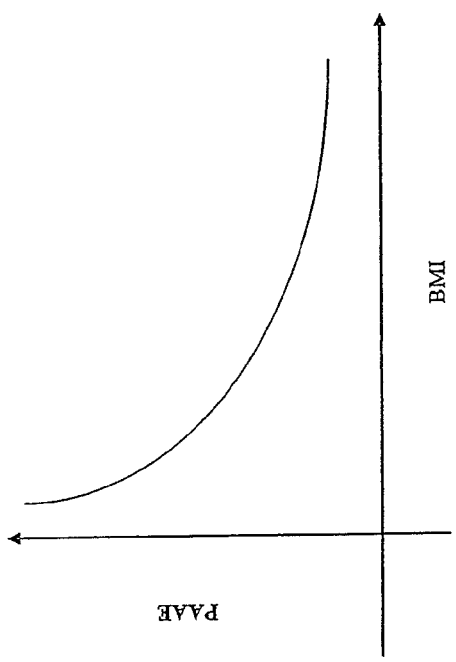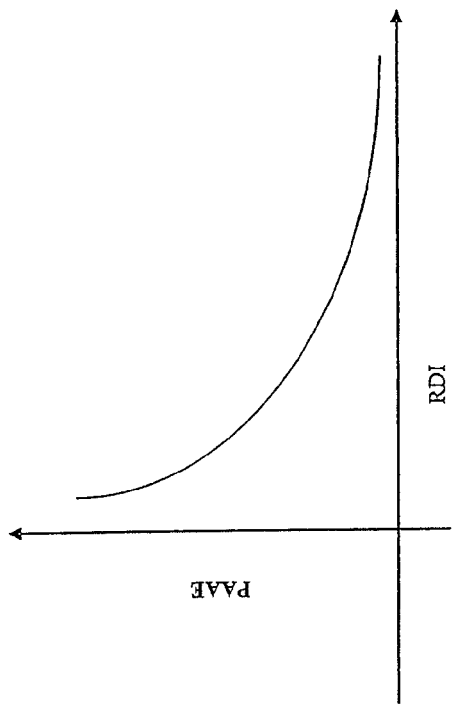

STEREOVIDEOSCOPE AND METHOD OF USING THE SAME

CROSS REFERENCE TO RELATED APPLICATIONS

This application is a national stage application filed under 35 U.S.C. 371 of International Application No. PCT/US2007/069025, filed May 16, 2007, which claims priority from U.S. Provisional Application No. 60/747,468 filed May 17, 2006, each of which is incorporated herein in its entirety.

BACKGROUND OF THE INVENTION

1. Field of the Invention

The present invention is related to the field of visual inspection in the medical and dental environments, and more particularly, to a stereovideoscope and a method of using the same for providing data associated with a portion of a patient's anatomy (particularly providing images for measurement during upper airway evaluation).

2. Description of Related Art

Obstructive sleep apnea (OSA) has been found to be as common as diabetes, asthma, and hypertension. Like those multi-systemic problems, OSA affects a large percentage of the population. However, with proper diagnosis and treatment, patients can live a normal life, and life-threatening risks are reduced.

The prevalence of OSA has been estimated to be 20% in the world's adult (25+ years of age) population (or approximately 660 million), with approximately 7% of all adults (~230 million) suffering from moderate to severe forms of the condition. The estimated incidence of mild OSA is even larger (estimated ~400 million). In the USA alone, an estimated 1 in 5 (~40 million) adults suffer from some form of OSA, with 1 in 15 (~15 million) adults having moderate to severe forms of OSA. The awareness and diagnosis of OSA are growing. Analysts estimate that fewer than 4% of OSA sufferers are currently diagnosed and being treated. This "undiagnosed patient gap" has created one of the fastest growing segments of the medical device industry, and this percentage is forecast by analysts to increase to over 24% by 2012.

Driving market growth coupled with an aging population (OSA risk increases over 40 years of age) have increased awareness of the public and the media and diagnosis by physicians. OSA is considered a risk factor for stroke and congestive heart failure, indications that are currently being studied in multicenter clinical trials.

There is no known cure for obstructive sleep apnea. Behavioral treatments such as weight loss and alcohol avoidance may be helpful, but are not always completely effective therapies. Surgical procedures are considered second line therapies and current surgical modalities result in inconsistent results. While airway pressure treatment is considered to be the first line of therapy worldwide (and has proven to be the most successful therapy in maintaining an open airway), this form of treatment suffers from a significant incidence of side-effects, and there is an equally significant lack of long-term patient compliance. The competitive environment for OSA therapeutic devices can be segmented into three main categories based upon treatment methods: nasal mask continuous positive airway pressure (CPAP), passive mandibular advancement oral appliances (OAT), and active oral positive airway pressure devices.

For nearly all patients diagnosed with some form of OSA, the most prescribed treatment (80% of all prescriptions) is a nasal mask plus air flow generator machine for the delivery of nasal CPAP, variable pressure Bi-level, or Auto-titration ("smart") CPAP systems to "splint open" the airway allowing air to flow freely to the lungs during periods of airway occlusion. CPAP systems have been found effective in treating mild, moderate, and severe cases of OSA and are considered the gold standard treatment modality.

Problematic to this form of treatment, however, is non-compliance. The American Sleep Disorders association estimated in 1993 that approximately 50% of patients prescribed CPAP systems were non-compliant (i.e., use of CPAP less than 4 hours per night). Non-compliance is the extreme manifestation of patient dissatisfaction with nasal CPAP; even compliant patients are not satisfied, as evidenced by the wide range of problems encountered by all users of nasal CPAP mask systems (e.g., nasal stuffiness, mask leak, dry throat, cold air stream, mask rubbing, more frequent awakenings, red/sore eyes, and nosebleeds).

Major factors in non-compliance are bulkiness, discomfort, and leakage problems inherent in the nasal mask CPAP systems. The number one complaint by OSA patients is the discomfort caused by their nasal mask. Poor training and follow-up from the device distributor, claustrophobia, nasal congestion, discomfort, complications with headgear adjustments, and nasal and skin allergies are also problematic. Excessive sinus irritation, injury, or physical deformities make nasal CPAP impractical. CPAP use is also associated with a limitation on the part of the patient to sleep in varying body positions while connected to the device; CPAP users are required to sleep only on their back or sides (they are unable to sleep in the prone position, i.e., on their stomachs). Patient health, public safety, and economic productivity all suffer when OSA patients fail to comply. All of these factors combined often promote seeking of alternative forms of treatment for this disorder, as described below.

Passive Dental Mandibular Advancement Appliances (OAT) affect advancement of the lower jaw, and are used to reposition the tongue in the oropharyngeal cavity to create a larger air passageway. These devices are useful as a primary treatment in a large percentage of cases of snoring and mild-moderate OSA (and in some isolated cases of severe OSA) and are often useful in cases of persistent apnea following failed soft palate or other upper airway surgery. Sleep physicians, general dentists, oral & maxillofacial surgeons, other dental specialists, and otolaryngologists often prescribe this treatment.

Based upon recent studies, a newly published Practice Parameter Paper produced by the American Academy of Sleep Medicine has added substantial credibility to this form of treatment, as numerous recent Level I and II studies have significantly elevated the level of knowledge surrounding use of these appliances and verified efficacy of this treatment. In particular, the American Academy of Sleep Medicine has revised its previously published practice parameters to now recommend first-line use of oral appliances in mild to moderate OSA (in those patients who prefer oral appliances to CPAP, or who are intolerant to CPAP therapy). Importantly, Level I evidence exists which suggests that OAT therapy is more effective than soft palate surgery in patients with mild-moderate OSA, and it is expected that prescriptions for this form of treatment will increase in the future.

Side-effects of OAT include potential changes in dental occlusion, Temporomandibular Joint symptom exacerbation, and current lack of capability to specifically predict who will respond best to this treatment.

Active Oral Positive Airway Pressure (OPAP) devices deliver positive pressure airflow via the oral cavity (bypassing the nasal airway). OPAP incorporates mandibular advancement and positive pressure ventilation, while other masks (such as the Oracle mask) deliver positive pressure ventilation alone without incorporating mandibular advancement. Minimal long-term data are available with this technique, and airway drying (despite the use of humidified circuits) is problematic.

Pharmacologic treatments for OSA have been ineffective. The fundamental cause of OSA is anatomically related and not impacted biochemically.

Various surgical techniques have been developed to treat OSA. Uvulopalatopharyngoplasty (UPPP) treatment includes resection of the uvula and portions of the soft palate to widen the oropharyngeal space. Although snoring is temporarily relieved in most cases, apnea often persists due to continued tongue-base narrowing. The overall success rate of UPPP is about 40% for primary snoring, but less for apnea (problematic is that many physicians fail to obtain objective sleep study data either before or following performance of this procedure, and a "silent apnea" situation is often created). Velopharyngeal incompetence and pharyngeal stenosis are significant complications to all forms of soft palate surgery.

Laser-Assisted Uvulopalatopharyngoplasty (LAUP) performs a similar result as the above utilizing a $CO_2$ laser. Laser treatment may worsen the respiratory disturbance index (RDI) and can cause long-term sequelae of a scarred airway. While snoring may be diminished, the diagnosis of OSA may be delayed because the primary symptom of OSA, i.e., snoring, is eliminated.

Genioglossus advancement procedure (GBAT) includes advancing the genioglossus attachment to the mandibular symphysis forward and fixating the same with plates and/or screws. Importantly, the long-term results of this technique are unknown, and clinical data surrounding the use of this technique are limited as it is often performed at the same time soft palate surgery is performed.

Maxillomandibular Advancement (MMA) has proven effective at reducing snoring and OSA in patients that have failed other therapies and who have clear anatomical abnormalities warranting a more intensive intervention. This procedure involves surgical repositioning of the upper and lower jaws. While the surgical literature suggests that this procedure has the greatest impact on affecting volumetric expansion at multiple areas of the upper airway (and is considered the most successful surgical procedure outside of tracheostomy for treatment of OSA), changes in facial appearance in addition to cost, complexity, and inconvenience have prevented this procedure from gaining wide acceptance.

Tracheostomy is typically the most effective and definitive surgical therapy for OSA. The oropharynx obstructed in OSA is simply bypassed by creating a hole in the trachea and inserting a tube to maintain a patent airway. This therapy has become less common due to the success of CPAP, and significant social stigma prevents the widespread use of this technique for most patients.

Radiofrequency (Somnoplasty) induces thermal lesions in the palate (for primary snoring) or tongue-base (for patients with OSA) which subsequently scar and resorb. This technique has not proved effective for OSA, as the majority of patients exhibit narrowing below the level at which the lesion is placed, and a relapse of snoring is typically seen 1-2 years following soft palate application in patients with primary snoring.

Injection Snoreplasty and scar-tissue inducing implants, like radiofrequency, induce scarring of the soft palate. While some temporary benefit is seen in patients with primary snoring and milder forms of apnea, recurrence of symptoms is often seen, and little (if any) long-term data is currently available.

Tongue-Suture techniques (Repose) utilize a nonresorbable suspension suture to advance the hyoid or tongue base; little (if any) long-term data related to this technique is currently available.

Clinicians, however, often offer a "shotgun" approach to all-corners with OSA (i.e., oral appliances are fabricated for all-corners), and no specific technique or mechanism is utilized in order to predict a given individual's probability of response to therapy (prior to appliance fabrication and initiation of treatment). As an alternative, clinicians often rely upon resolution of symptoms (after titration has been performed) as a means to judge response to therapy, but this is performed only after the appliance has been fabricated and treatment initiated. Unfortunately, beyond the generalized guidelines listed above, clinicians are currently unable to predict in advance which individuals will uniquely respond to OAT treatment and, therefore, who are the most appropriate candidates for this form of OSA therapy.

Similarly, surgeons involved in performing mandibular advancement (or tongue-base) surgery in patients with OSA currently have no means of predicting how far the mandible (or tongue base) must be advanced in any given individual in order to affect a cure of upper airway obstruction. This inability to predict response to therapy often leads to inappropriate appliance fabrication and/or inappropriate or inadequate surgical advancement in patients who will not, by reasons of anatomical expansion or physiologic improvement, respond to therapy.

While mandibular protrusion/advancement is the basic mechanism implemented by OAT, it is generally accepted that oral appliances work by affecting both anatomic expansion of the tongue-base region and physiologic reduction of soft tissue compliance (of the upper airway) during sleep. While obstruction is accepted to be a dynamic (or non-fixed) process, anatomic expansion in this case (per Poiseuille's Law) refers to the ability to expand the most critical (or stenotic) site of proximal narrowing of the upper airway (MCSPN) above the glottic opening. Per Poiseuille's law, small changes in the radius of the tube at its narrowest point affect exponential changes in airflow (the radius in this equation is raised to the fourth power). For example (all else being equal) according to Poiseuille's law, doubling the radius of the tube at its narrowest point increases airflow by a factor of sixteen.

It would therefore be advantageous to provide a system and method of providing objective data to predict the efficacy of tongue-base therapies, such as various nonsurgical and surgical tongue-base therapies, the response to both OAT treatment, and mandibular advancement surgery in patients with OSA. Moreover, it would be advantageous to provide a system and method for generating such predictions in a user-friendly and reliable manner.

BRIEF SUMMARY OF THE INVENTION

The present invention addresses the above needs and achieves other advantages by providing a system, method, and computer-readable medium for predicting the efficacy of tongue-base therapies. Embodiments of the present invention provide the capability to utilize airway measurements as obtained from a variety of awake or asleep upper airway measurement techniques to determine a probability of a positive response to a tongue-base treatment, such as the response to OAT and mandibular advancement surgery in patients with OSA. As such, embodiments of the present invention provide the probability of a patient's response to various tongue-base treatments based on objective data.

According to one embodiment of the present invention, a method for predicting a response to tongue-base therapies is provided. The method includes generating a plurality of images of at least a portion of a patient's anatomy (during either wakefulness or sleep states), acquiring data indicative of the portion of the patient's anatomy from the images, and determining a probability of a response of the patient to a tongue-base treatment based on the acquired data. For example, the method could determine the probability of a response to treatment for obstructive sleep apnea, such as OAT treatment, tongue-base directed therapies, and mandibular advancement surgery. In an additional embodiment, a computer-readable medium containing instructions may be constructed for causing a processing element to perform the method described herein.

Various aspects of the method include generating supine hypotonic images of an upper airway of the patient with the patient's head and neck in a neutral standard position. In addition, the generating step may include generating at least one image of an airway with the mandible at rest and the mandible at an advanced position, while the acquiring step may include acquiring an image of an anterior/posterior measurement and/or a lateral measurement of a most critical site of proximal narrowing of the upper airway (MCSPN) with the mandible at rest and the mandible at the advanced position. The acquiring step could further include acquiring an area of a MCSPN of the airway at rest and the mandible maximally advanced, as well as acquiring a percentage area airway expansion (PAAE).

Moreover, additional aspects of the method include inputting patient-specific data, such as body mass index, respiratory disturbance index, apnea hypopnea index, age, neck circumference, and/or gender. The method could also include displaying the probability of a response as at least one graphical image. The method may further include capturing data indicative of at least a portion of a patient's anatomy, and subsequently generating the at least one image based on the captured data.

A further embodiment of the present invention provides a system for predicting a response to tongue-base therapies. In particular, the system includes a stereovideoscope for capturing data indicative of at least a portion of a patient's anatomy, and a processing element. The processing element is in communication with the stereovideoscope and is configured for generating images based on the captured data, acquiring data indicative of the portion of the patient's anatomy from the images, and determining a probability of a response of the patient to a tongue-base treatment based on the acquired data. According to one aspect of the system, the processing element comprises a graphical user interface for displaying the image(s). The graphical user interface may also be capable of displaying an image representative of the probability of a response.

A further embodiment of the present invention provides a measurement method including taking stereoscopic images with a stereoscope of a patient lumen, determining three-dimensional measurement(s) of the lumen and comparing the measurement(s) to a standard or other measurements for the lumen.

A further embodiment of the present invention provides a device for acquiring data associated with a portion of a patient's anatomy (e.g., an upper airway of the patient). The device includes a scope including a plurality of stereoscopic lenses for acquiring data associated with at least a portion of the patient's anatomy. The device is coupled to a distal end of a flexible tubing, wherein the flexible tubing comprises a biocompatible material. Moreover, at least a portion of the device is capable of being subjected to a sterilization process. The scope may be interchangeable or permanently fixed to the distal end of the flexible tubing. The device is capable of capturing images associated with the patient's anatomy such that various geometrical measurements may be acquired therefrom (e.g., distance, point-to-line, angular, area, depth, and profile measurements). According to one aspect of the present invention, the device is configured to acquire images associated with an upper airway of the patient such that the acquired measurements may be used to determine a probability of a patient's response to a tongue-base treatment.

Embodiments of the present invention may have many advantages. For example, the present invention may provide a cost effective technique for determining the probability of response to various tongue-base therapies. In addition, methods of the present invention may be performed efficiently, are non- or minimally invasive, and practical (easily utilized in an average clinician's private office). Embodiments of the present invention may allow direct measurement of the upper airway during the awake or supine REM sleep state, are easy and comfortable for the patient, and reliable. Embodiments of the present invention may also enable rapid measurement of MCSPN volume during both supine (maximally protruded mandibular position) and hypotonic supine (mandible at rest) positions of the mandible, as well as rapid calculation of probability of the success/failure at a defined RDI level. Furthermore, once individual patient-specific variables (RDI, BMI, age, and/or gender) are entered into the processing element by the clinician, and objective airway measurements performed, calculation of the probability of treatment success is then performed by the processing element, and the clinician and patient will then be able to proceed based upon objective information. The stereovideoscope facilitates the collection of objective data that may be readily used to provide more accurate and reliable measurements associated with a portion of the patient's anatomy.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 5 is a graph illustrating the expected relationship between body mass index and percentage volumetric airway expansion;

FIG. 6 is a graph illustrating the expected relationship between respiratory disturbance index and percentage volumetric airway expansion;

DETAILED DESCRIPTION OF THE INVENTION

Figure 1:
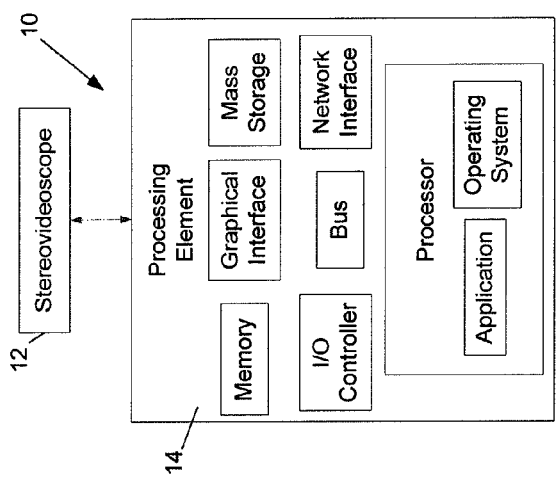
FIG. 1 depicts a system for predicting the response to tongue-base therapies.

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Until recently, the American Academy of Sleep Medicine has utilized severity of disease to suggest those groups of patients who may respond best to therapy with oral appliances, but these guidelines serve as general predictors only, as a given individual's unique response to treatment (even in mild-moderate cases) is currently unpredictable. For instance, many patients with mild-moderate OSA who attempt treatment with OAT may fail to obtain a therapeutic reduction of the Apnea Hypopnea Index (AHI) or Respiratory Disturbance Index (RDI) even after full appliance titration.

When the MCSPN shows adequate expansion with forward posturing (or advancement) of the mandible, a favorable response to OAT therapy is often seen (i.e., when a critical area (CAAE) or volume of airway expansion (CVAE) or more specifically, a critical percentage of airway volumetric expansion (PVAE) at MCSPN is achieved, effectiveness of OAT is improved). Unfortunately, clinicians do not currently have a practical means to evaluate MCSPN or PVAE during mandibular protrusion (either in the awake, or sleep state) and, therefore, the ability to predict who will respond therapeutically to OA therapy is problematic. PVAE (enough to attain CVAE) will vary, based upon the presenting baseline hypotonic MCSPN size, body mass index (BMI), age, gender, neck circumference, and presenting RDI.

Further complicating this problem is that there is not a direct linear relationship (even in patients with mild-moderate OSA severities) between degree of mandibular protrusion and degree of expansion of the upper airway at MCSPN (i.e., in some individuals who are able to protrude the mandible only a small amount, a large degree (or percentage) of expansion may occur. However, the opposite is also true: some patients who protrude the mandible quite far may exhibit minimal or no degree of airway expansion.

Based upon polysomnographic calculation of the AHI, it is accepted that the more elevated the AHI, the more diffuse soft tissue collapse occurs (i.e., higher soft tissue compliance (STC) is seen in patients with more severe OSA, while lower STC is seen in milder forms of OSA). This anatomic region of airway narrowing is not able to be easily accessed, identified, or measured during routine intra-oral or extra-oral clinical exam. Awake lateral cephalometry (utilizing a barium-swallow technique at end-expiration) may allow assessment of the pattern of airway narrowing, but is taken in the upright position and is not widely used. Awake acoustic pharyngometry has been suggested as a means of evaluating STC, airway measurements, and airway expansion; however, practical use of this technology has proven difficult as technical difficulties acquiring a consistent waveform are often encountered, precise anatomic relations cannot be identified, measurements are obtained during wakefulness, and interpretation of generated clinical data is often ambiguous (no predictive capability is attained with this device).

Critical closing pressure (Pcrit) is also higher in OSA patients than normal patients (less negative pressure is required to affect airway closure in OSA patients than in normal patients). Calculation of Pcrit is confined to specialized institutional research facilities, and simple anatomic localization of airway narrowing can prove problematic.

Awake supine and/or upright endoscopic evaluation of the upper airway (utilizing a hypotonic technique, and with the airway size evaluated both with the mandible at rest and maximally advanced) has been performed for many years; without a means to objectively measure endoscopic changes in upper airway volume, however, the resulting subjective exam is prone to examiner bias and is not considered reliable (and once again, is typically performed during wakefulness). Anesthetically-sedated (and nocturnal endoscopy) has also been reported, but this is not commonly performed (certainly not under the conditions of monitored polysomnography) and suffers from the same subjective bias. Intra- and inter-examiner reliability (based upon published kappa values) is low with this subjective technique.

A PVAE (to CVAE), as defined by resolution of the AHI (thereby lowering Pcrit and STC) in relation to mandibular advancement and the MCSPN is needed in patients with OSA to eliminate upper airway obstruction. This PVAE may or may not be reached for any given individual via mandibular protrusion, as MCSPN expansion is not necessarily linearly related to the amount of mandibular protrusion (the actual amount, or distance, of maximal mandibular protrusion varies between patients, and the amount of mandibular protrusive range of motion is only important in relation to the OA titration). It is generally assumed, however, that the lower the presenting RDI and BMI, the more linear this relationship between mandibular advancement and AHI becomes.

Airway size (for a given individual) is also a factor of genetics and environmental influences, and the degree of MCSPN expansion (or PVAE) during mandibular protrusion may be affected by age, gender, and the ability of the patient to protrude the mandible.

Airway size may actually diminish with age and weight gain, as the associated soft tissues become more compliant, and centrally-driven muscular dilation is unable to compensate for the added soft tissue load/burden. Increased BMI is also often associated with smaller and more collapsible airways, as added adipose burden on the upper airway dilator muscles prevents adequate dilation and maintenance of MCSPN during the sleep state (particularly during supine REM sleep). By definition, increased AHI is related to increased susceptibility to obstruction. Finally, males (it is felt) are generally more susceptible to obstruction than females (although this is not always so), possibly reflecting a protective hormonal effect (at least until menopause) in females.

As opposed to guidelines focusing on generalized groupings of large numbers of patients, new technologies and techniques which permit calculation of PVAE of the upper airway at MCSPN (initially [for OA therapy] from mandibular retruded (hypotonic) to maximally (tolerable) protruded (or advanced), but also comparing any pretreatment to posttreatment tongue base expansion method or technique), while additionally accounting for variables of RDI and BMI, age, and gender will allow calculation of probability of response to tongue-base therapies in individual patients with OSA. The most immediate application of this idea is to predict probability of response to therapy with oral appliance therapy.

A tool which allows measurement of MCSPN and PVAE in relation to mandibular protrusion during the wake state, but which also factors the difference in percentage of airway closure during sleep and variables noted above, would be of benefit in predicting response to therapy in individual patients (i.e., probability of response) over the range of an individual's range of mandibular protrusion, and thereby lead to more efficient and appropriate application of OA and surgical mandibular advancement therapy to the OSA population (thus, more efficient and practical use of health-care financial resources).

While evaluation of MCSPN and PVAE during supine wakefulness may allow a more straightforward exam process (and avoids the technical difficulty of evaluation during sleep state), complicating this calculation is the fact that for MCSPN sleep state volumetric size often differs from that seen during wakefulness. This diminution in airway size during supine REM sleep (the most vulnerable body position and stage of sleep) should be accounted for in any therapeutic or predictive process.

Positional influences of supine versus non-supine sleep also add further complexity, as supine sleep is recognized to be the most vulnerable position for airway obstruction. Prior studies have shown that pharyngeal length can be altered by longitudinal tension. An elongated pharynx (as produced through cervical extension) based on traction forces has been shown to have less collapsibility than a shorter (more compliant) airway. Pharyngeal length as defined in the seated position (as often is utilized with the acoustic pharyngometry technique) could arguably be under different mechanical forces based on gravitational and long volume tethering effects as compared with the supine position, thereby causing distortion of the measurement. It can be assumed, however, that for any given upright or supine hypotonic MCSPN noted during the wake state, this same anatomic location/site will be smaller during supine hypotonic REM sleep, as dilating muscle activity abates during this phase of sleep. The degree of cervical flexion/extension during required measurements for this device are accounted for and controlled as defined below.

Genioglossus muscle tone in the supine position is augmented during the awake state, but lost during sleep (for this reason, acoustic pharyngometry is often performed in the upright position, in order to minimize this influence of augmented muscle tone). This effect may be noted endoscopically in some, but not all patients.

Inherent to any discussion regarding treatment success (or probability thereof) must take into consideration the definition of success (which in this case, is the reduction of RDI to 10 or less).

As opposed to subjective evaluation, cephalometry, acoustic reflection, fluoroscopy, endoscopy, ultrasound, CT, and MRI have been employed for evaluation of the upper airway as a means of viewing and/or measuring upper airway volume. Small diameter scopes (e.g., 4 mm or less) currently used for upper airway endoscopic evaluation do not include stereoscopic lenses, which limits the ability to obtain accurate and reproducible measurements. While measurements utilizing these (and other) techniques form the basis for predictions to response to treatment, limitations to these techniques relate to the inability to assess the airway in the hypotonic (i.e., end-expiration) supine REM sleep state, slow scan times, and financial practicality.

New technologies are currently available that allow for objective instantaneous endoscopic measurements. Endoscopy (while one of many technologies allowing airway measurements) can be considered as a foundational tool for this technique, as endoscopy is often performed by otolaryngologists, oral & maxillofacial surgeons, and pulmonologists and, hence, widely available (general dentists who offer treatment for OSA may also begin offering this service). These new technologies for objective endoscopic measurements, however, have not been widely applied to the medical arena, as most uses have been in various industrial settings (i.e., aerospace and utility industries).

Generally, embodiments of the present invention provide a stereovideoscope for use in methods for predicting the efficacy of tongue-base therapies, such as (but not limited to) the response to both OAT treatment, surgical and non-surgical tongue-base therapies, and mandibular advancement surgery in patients with OSA. In particular, embodiments of the present invention include generating images of the upper airway, acquiring data from the images, and using this data in conjunction with an algorithm to generate the probability of response to a particular treatment for a patient, such as treatment to OSA.

As will be explained in further detail below, once an individual patient's data for percentage of airway expansion is determined (by one of various measurement technologies), patient specific data is also input (such as BMI, RDI, neck circumference, age, and/or gender), and a processing element and associated software then computes the patient-derived data in relation to a probability curve (generated as a result of study of a large reference population of patients). Where the individual patient's data falls in relation to the curve then determines an individual patient's probability of response to a particular tongue-base therapy. Moreover, derivation of the critical airway expansion (according to a given patient's BMI, age, gender, and/or RDI) can also allow calculation of how much forward movement of the mandible/jaw/tongue base is needed in any given individual for an anticipated surgical procedure. As such, methods of the present invention allow clinicians to objectively and more reliably predict which patients are candidates for OSA treatment.

Although reference is made herein to predicting the response to OSA treatment, it is understood that the present invention is capable of predicting the response to various tongue-base therapies. In this regard, the present invention may be employed to predict other responses to treatments, as well as for diagnostic purposes. For instance, the present invention could be used for predicting the response to surgical therapy, response to hyoid suspension techniques, tongue-base suture suspension techniques, radiofrequency techniques, genioglossus advancement, and mandibular advancement techniques.

One embodiment provides a system 10 for carrying out methods of the present invention. FIG. 1 illustrates a stereovideoscope 12 that is in communication with a processing element 14. The stereovideoscope 12 could be directly connected to the processing element 14 or remotely communicate therewith, such as via wireless or network communications. The stereovideoscope 12 preferably communicates captured data to the processing element in real time, although batch processing could be implemented if desired. Thus, the data could include video, still images, and/or audio information associated with the portion of the patient's anatomy being inspected that may be output to a user, such as via a graphical interface, as explained in further detail below. The stereovideoscope 12 may also be portable. For example, the stereovideoscope 12 may be configured to be worn around a physician's neck and be battery operated.

The stereovideoscope 12 generally includes a flexible tubing extending between a processing element 14 and a scope having a plurality of lenses. In particular, the stereovideoscope 12 utilizes stereoscopic lenses (of adequate focal lengths to insure accuracy of measurements) in order to capture images for readily acquiring measurements from images in multiple directions. For example, the scope may include a CCD camera and stereoscopic lenses for capturing images.

The flexible tubing may be any suitable length and diameter for accessing a variety of locations within the patient's body and providing a conduit for communication between the scope and the processing element 14 (e.g., fiber optic cables). According to one aspect of the present invention, the diameter of the tubing is less than 5 mm. The scope may be permanently attached to the distal end of the tubing or may be interchangeable for different scoping applications if desired.

Moreover, the stereovideoscope 12 is capable of capturing images indicative of portions of the anatomy, such as the upper airway shown in FIG. 2. In addition, the stereovideoscope 12 is capable of obtaining images such that distance, point-to-line, angular, area, depth, and profile measurements may be readily acquired for upper airway evaluation. For example, images captured by the stereovideoscope 12 could be employed to acquire a measurement of the upper airway with the head in a neutral supine reference position. In addition, images acquired by the stereovideoscope 12 are capable of providing three-dimensional data of the upper airway. Thus, using stereo measurements (to allow measurements from non-perpendicular orientations) and simple geometric triangulation methods, various measurements can be objectively calculated at MCSPN while the mandible is at rest and compared to the same measurements while the jaw is maximally advanced (in order to derive a PVAE measurement).

According to one embodiment of the present invention, the device could be similar to an IPLEX® videoscope manufactured by Olympus Optical Co., Ltd or a videoscope manufactured by GE Inspection Technologies. However, such devices are not compatible for use within the medical or dental environment. As such, the stereovideoscope 12 is adaptable for use within the medical or dental environment and includes a biocompatible material that covers or comprises the flexible tubing. Thus, a sheath or coating of biocompatible material could be applied to the outer surface of the flexible tubing, or the flexible tubing could be fabricated of biocompatible material. The biocompatible material could be a polymeric material or combinations of polymeric materials. For example, the material could be a silicone, polyurethane, or polytetrafluoroethylene (e.g., Teflon®) material. In addition, portions of the stereovideoscope 12 that are placed within the patient's body are preferably capable of being sterilized (e.g., cold sterilization such as EtO) for use in various medical or dental procedures.

Although the stereovideoscope 12 has been discussed in conjunction with capturing images of an upper airway, it is understood that the stereovideoscope is capable of being utilized for capturing images of various areas associated with a portion of a patient's anatomy within the medical and dental environments. Moreover, the stereovideoscope 12 may be various diameters and lengths depending on the particular portion of the patient's anatomy to be inspected. In addition, the stereovideoscope 12 may include one or more additional features for facilitating the collection of data such as a working channel extending through the flexible tubing to its distal end, a light source proximate to the scope to increase visibility of the scope, and/or a device (e.g., forceps) attached proximate to the scope for performing a medical or dental procedure. The scope is also capable of being controlled via a user to position the scope for capturing an image (e.g., pan or change the orientation of the scope).

The processing element 14 may include any number of conventional hardware and software components, as depicted in FIG. 1. For example, the processing element could include memory (e.g., RAM), mass storage (e.g., magnetic hard disk or optical storage disk), I/O controller, network interface (e.g., Internet, intranet, or extranet), bus for transferring data or power between processing element components or between processing elements, data card(s), and/or a graphical interface. The graphical interface, as known to those of skill in the art, provide methods for displaying and interacting with images generated in response to data captured by the stereovideoscope 12 onto a monitor or similar viewing device (e.g., LCD monitor).

In addition, the processing element includes a processor that could include one or more applications (e.g., programs) and a standard operating system. Thus, the stereovideoscope 12 is typically operated under the control of software contained in the processing element 14. The software could be contained on one or more data cards, where each data card corresponds to a particular stereovideoscope 12. The data cards could be used for interfacing with various hardware and software components residing in the processing element 14, as well as storing various data associated with each stereovideoscope 12, such as to account for optical aberrances. The processing element 14 may be a computer, such as a personal computer or workstation, although the processing element could be any device capable of performing methods of the present invention, such as a monitor or a portable device, such as a laptop, a personal data assistant, or mobile phone. Furthermore, the stereovideoscope 12 could be in communication with one or more processing elements 14, and the processing element is capable of communicating with other processing elements residing in a network.

As mentioned above, the processing element 14 is capable of displaying images in real time such that a video of the captured data may be shown, or still photographs may be taken at any time in order to acquire data directly from the graphical interface or from a printout of the image. However, it is also understood that the stereovideoscope 12 could collect data at pre-determined times, rather than sending real-time data to the processing element 14, and send the data to the processing element for display by the graphical interface or for output by an output device, such as a printer. Therefore, although a graphical interface is preferred, it is possible to incorporate the processing element 14 without a display and to instead provide a printout of the image(s), or to utilize any other technique for viewing images of the captured data and acquiring data from the images. The processing element 14 is capable of maintaining a permanent record of the captured data and images for future use or record keeping, which allows a user to store and edit previously created images.

Figure 2A:
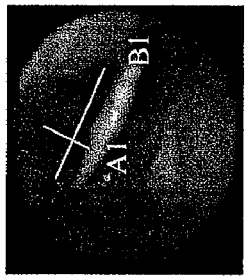
FIGS. 2A-2D illustrate endoscopic views of the upper airway of a patient.
Figure 2B:
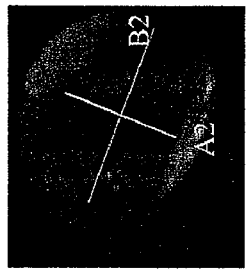
Figure 2C:
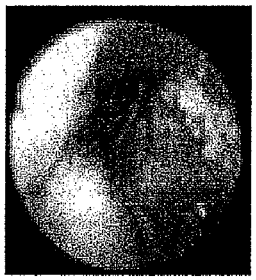
Figure 2D:
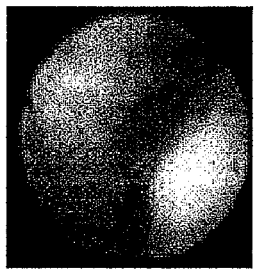

FIGS. 2A-2D and 3A-3B illustrate images of the upper airway captured by the stereovideoscope 12 and generated by the processing element 14, which are used to acquire various measurements according to one embodiment of the present invention. Thus, the processing element 14 is capable of using a graphical user interface to acquire various measurements on the displayed image (e.g., distance, area, and volume). In this regard, FIG. 2A illustrates an image of a hypotonic supine upper airway endoscopic view (mandible at rest/retruded position) taken during either supine REM sleep or during the supine awake state (with the head/neck in a neutral standard reference position), where A1 corresponds to an anterior-posterior measurement of the MCSPN (from posterior pharyngeal wall to epiglottis tip), and B1 corresponds to a lateral measurement of the MCSPN (widest aperture in lateral dimension). FIG. 2B depicts an image of a supine upper airway endoscopic view with the mandible maximally advanced, where A2 corresponds to the MCSPN with the mandible at a maximally advanced position, and B2 corresponds to the lateral airway with the mandible at a maximally advanced position. Furthermore, FIG. 2C shows an image of the Mueller maneuver, and FIG. 2D illustrates an image of the retropalatal endoscopic view. The anterior-posterior change is calculated as: $(A2-A1/A1\times100)-PAAC=PAAE_{AP}$, where PAAC is percentage of area airway collapse and PAAE is the percentage of area airway expansion, and the lateral change is calculated as:

$$(B2-B1/B1\times100)-PAAC=PAAE_{lateral}.$$

Figure 3B:
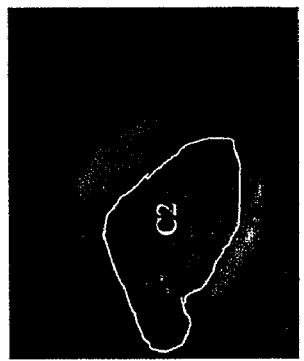
FIGS. 3A-3B illustrate endoscopic views of the upper airway of a patient.
Figure 3A:

For clinical utility, any calculation of PAAE should account for the percentage of area decrease of the critical airway size that occurs naturally during sleep (i.e., PAAC), or the percentage of area airway collapse during sleep (i.e., percentage airway collapse that occurs in transition from wake to REM sleep). FIGS. 3A-B show that area changes can be calculated for the supine hypotonic upper airway endoscopic view with the mandible at rest (FIG. 3A), and for the supine upper airway endoscopic view with the mandible maximally advanced (FIG. 3B). Similarly, the area change for any given segment of the upper airway may be calculated using the following equation:

$$(C2-C1/C1\times100)-PAAC=PAAE.$$

It is understood that the general focus is on expansion of the narrowest portion of the tongue base (i.e., MCSPN), which is determined initially as an increase in area (i.e., linear measurements). In some patients, volumetric changes over a given segment of the airway will be required, therefore, incorporating a third dimensional factor. Therefore, linear, area, and volumetric measurements (e.g., PVAC and PVAE) may be readily made using the images generated by the processing element 14, and that data indicative of the upper airway may be acquired using the images.

PAAC (and PVAC) are constants that can be determined based upon objective airway measurements of a large group of reference patients during hypotonic supine awake and hypotonic supine REM sleep studies (again, using standard neutral reference head positions). Calculation of the PAAC (or PVAC) during the generation of the reference database will facilitate the creation of a constant, which (when factored into measurements made in any individual) will allow subsequent assessment in individual patients during the awake state. The reference database will also be assessed for treatment success to oral appliance therapy (i.e., tongue-base expansion).

The MCSPN of proximal upper airway narrowing during hypotonic supine REM sleep can be defined as the narrowest proximal (hypopharyngeal) portion of the airway (i.e., closest to, but above the glottis); the assumption is that for most (but not all) patients, the retroepiglottic airway segment is typically the MCSPN. In addition, the ability of the MCSPN to expand with any therapeutic maneuver (for example, maximal forward posturing of the mandible in patients with oral appliances) (defined as PVAE), during hypotonic supine REM sleep, as well as supine hypotonic awake state, and the variation in AHI or RDI resulting (during sleep) from these tested positions (in a large reference group of patients with sleep-related breathing disorders and OSA) can be defined. Sub-categorization of these groups based upon BMI, age, gender, and RDI can be implemented, and thereby permit calculation of a series of linear and nonlinear mathematical relationship curves (for example, the relationship of PAAE to BMI, age, gender, and/or RDI). Measuring the maximal comfortable forward position of the mandible and the resulting PAAE, when correlated to resulting BMI, age, gender, and presenting AHI or RDI allows the calculation of a CAAE. Furthermore, the percentage decrease in MCSPN volume (or size) from upright hypotonic wake to hypotonic supine REM sleep (based upon AHI or RDI spectrum from mild to severe) in a large reference group of patients with sleep-related breathing disorders can be defined in a similar manner. These measurements allow for creation of a series of mathematical relationships to compare sleep and wake states, and can be expressed as constants for a given presenting AHI, RDI, gender, age, and/or BMI. As such, each of these measurements and calculations can be derived from a study of a large reference population of patients and entered into a database. The resulting reference database can serve as the basis for the probability boxes, which are explained in further detail below.

Figure 4:
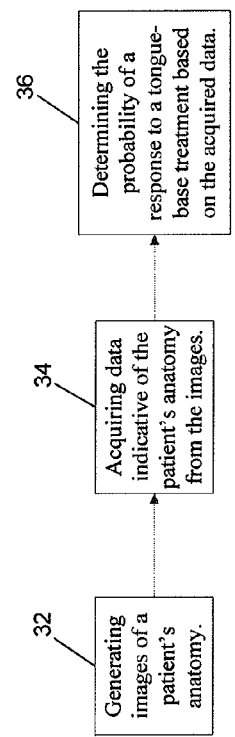
FIG. 4 is a flowchart of an exemplary method for predicting a response to tongue-base therapies.

Additionally, embodiments of the present invention can employ a multivariate algorithm to calculate the statistical probability of treatment success over a given range of airway expansion (from MCSPN airway volume measured at both mandibular retruded and maximally, i.e., comfortably, protruded) to a given PAAE, (while accounting for AHI, RDI, age, gender, and/or BMI based on the data acquired from the images, as well as the various parameters discussed above. Thus, the probability of treatment success for any individual will be based upon a comparison of patient-specific measurements to the reference database discussed above. In general, FIG. 4 illustrates that a method according to one embodiment of the present invention includes generating a plurality of images of a portion of a patient's anatomy (block 32), acquiring data indicative of the patient's anatomy from the images (block 34), and determining the probability of a response of the patient to a tongue-base treatment based on the acquired data (block 36).

For example, FIGS. 5-9 illustrate various exemplary datasets (and probability curves) generated by the system 10 of the present invention. In particular, FIG. 5 depicts an expected relationship between BMI and PAAE (similar curves could be generated for PVAE), while FIG. 6 shows an expected relationship between RDI and PAAE. PAAE is calculated using the above technique shown and described with respect to FIGS. 2A-2D and 3A-3B, as well as the various parameters described above, RDI (or Respiratory Disturbance Index) is known to those or ordinary skill in the art as the number of hourly apneas+hypopneas+respiratory effort-related arousals, and BMI is known to those of ordinary skill in the art as the measure of body mass based on height and weight of a patient. Thus, FIGS. 5 and 6 demonstrate that the expected relationship is non-linear, which indicates that the present invention is capable of correlating variables that are generally otherwise incapable of being reliably used to predict a given individual's response to tongue-base treatment.

Figure 7:
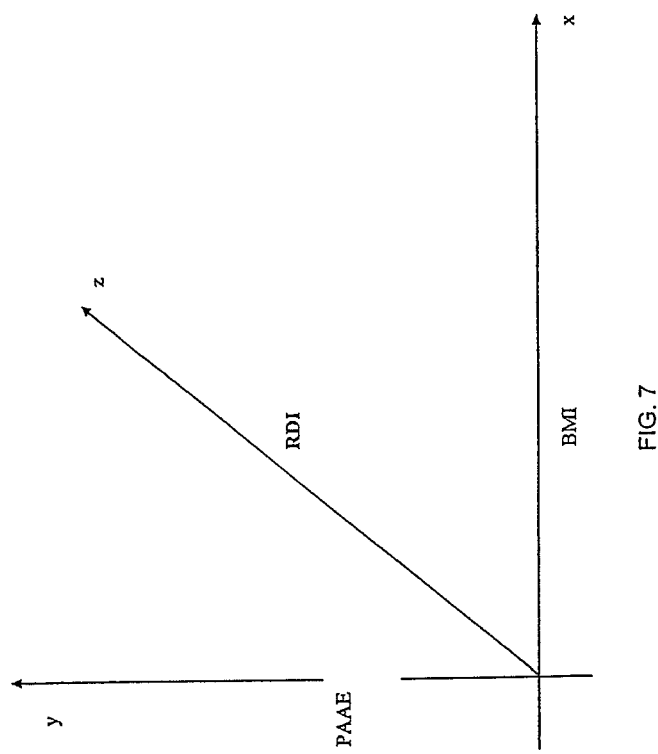
FIG. 7 is a graph illustrating the expected relationship between respiratory disturbance index, body mass index, and percentage volumetric airway expansion.
Figure 8:
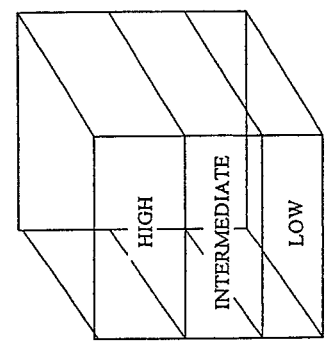
FIG. 8 is a perspective view of a probability box.
Figure 9:
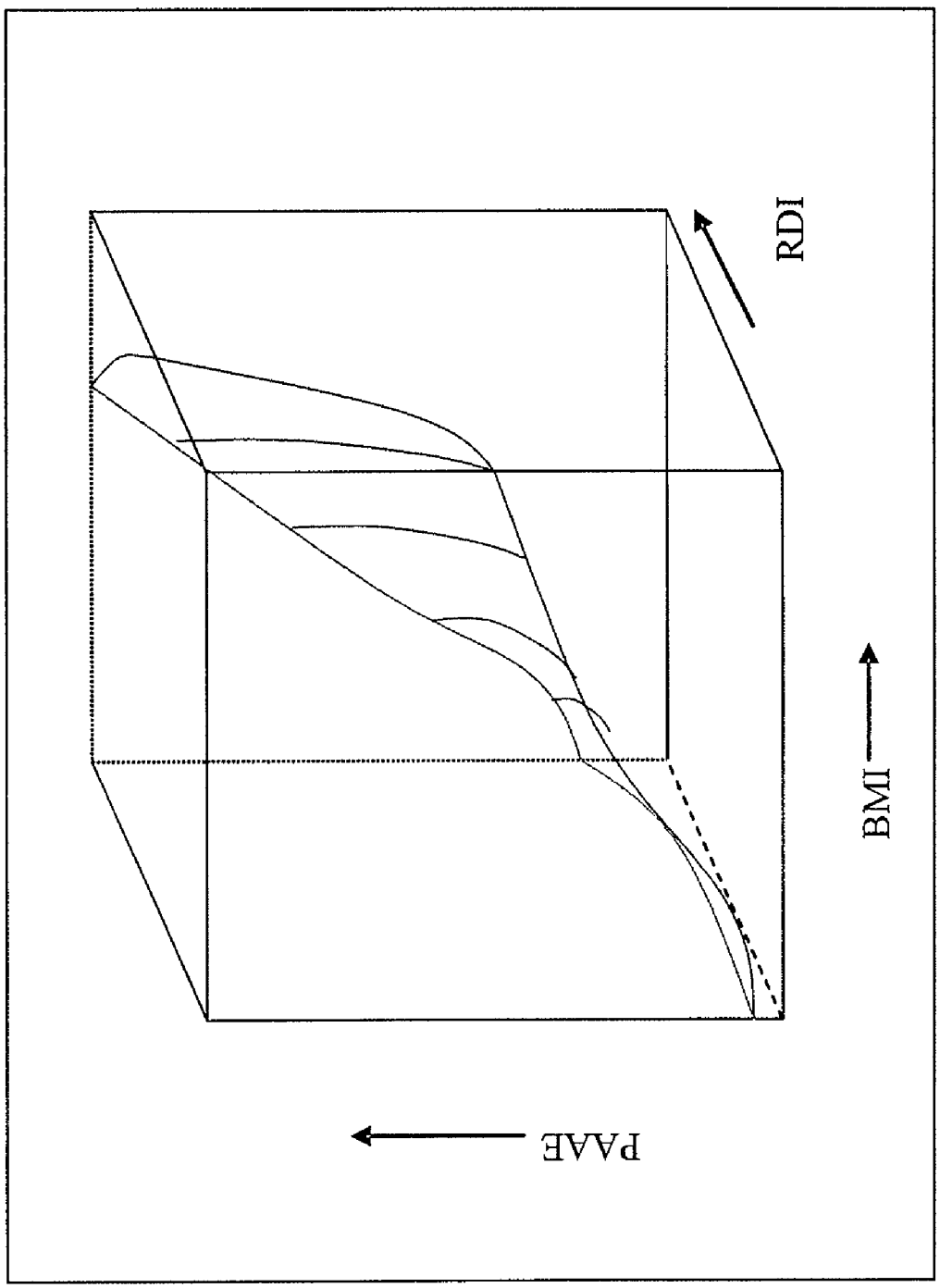
FIG. 9 is a perspective view of the expected relationship between respiratory disturbance index, body mass index, and percentage volumetric airway expansion plotted within a probability box.

Moreover, FIG. 7 illustrates the expected relationship between RDI, BMI, and PAAE in three coordinates. FIG. 8 depicts a probability box that includes low, intermediate, and high probability portions, and FIG. 9 shows an expected relationship between RDI, BMI, and PAAE shown in three-dimensional space within a probability box. Therefore, those points that fall above the curve shown in FIG. 9 would have a high probability of responding to tongue-base treatment, whereas those points that fall below the curve in FIG. 9 would have a low probability of responding to tongue-base treatment. Accordingly, those points that fall close to the curve would have an intermediate probability of responding to tongue-base treatment. Thus, given a specific patient's PAAE, BMI, age, gender, and RDI, a series of probability boxes and curves can be created which allow calculation of the patient's probability of response to OSA (tongue-base) treatment using FIG. 9. Mathematical calculation and description of the shape of the probability curve is performed based upon the reference data.

It is understood that cervical (neck) flexion and extension will shift the relative position of the curve within the probability box; flexion (compared with the standard neutral reference measurement position) will tend to cause a relative upward shift in the entire curve, thereby increasing the probability of treatment failure. Cervical (neck) extension (in relation to the standard neutral reference measurement), conversely, will tend to cause a downward shift in the entire curve, thereby increasing the probability of treatment success.

It is understood that several different probability boxes may be generated in order to better predict different patient's response to OSA (tongue-base) treatment. For instance, the same coordinates of BMI, RDI, and PAAE (defining the three axes of space) can be generated for a series of male patients of varying ages (or age groups), i.e., ages 20-30, 31-40, etc. Each of these curves may have a slight varying shape depending upon characteristics for this group of patients. Similarly, the same coordinates can be used to generate a series of probability curves for female patients of varying age groups, i.e., age 20-30, age 31-40, etc. Once again, each of these curves may have a slight varying shape so as to accurately reflect subtle differences in each grouping of these patients. As an alternative to RDI, AHI could be plotted along with BMI and PAAE in order to generate an additional or alternative curve within the probability box. It is also understood that the system 10 of the present invention is not limited to generating probability boxes and curves therein for predicting a response to tongue-base treatment. For example, the processing element 14 could generate and output a value (e.g., 90%), such as on the graphical user interface or with an output device, that corresponds to the probability of a patient's response to an OSA treatment.

According to one aspect of the present invention, the system 10 generally operates under control of a computer program product. The computer program product for performing the methods of embodiments of the present invention includes a computer-readable storage medium, such as the memory device associated with a processing element, and computer-readable program code portions, such as a series of computer instructions, embodied in the computer-readable storage medium.

In this regard, FIG. 4 is a control flow diagram of a method and program product according to the invention. It will be understood that each block or step of the control flow diagram, and combinations of blocks in the control flow diagram, can be implemented by computer program instructions. These computer program instructions may be loaded onto a processing element, such as a computer, server, or other programmable apparatus, to produce a machine, such that the instructions which execute on the processing element create means for implementing the functions specified in the block (s) or step(s) of the control flow diagrams. These computer program instructions may also be stored in a computer-readable memory that can direct the processing element to function in a particular manner, such that the instructions stored in the computer-readable memory produce an article of manufacture including instruction means which implement the function specified in the block(s) or step(s) of the control flow diagram. The computer program instructions may also be loaded onto the processing element to cause a series of operational steps to be performed on the processing element to produce a computer implemented process such that the instructions which execute on the processing element provide steps for implementing the functions specified in the block(s) or step(s) of the control flow diagram.

Accordingly, blocks or steps of the control flow diagram support combinations of means for performing the specified functions, combinations of steps for performing the specified functions, and program instruction means for performing the specified functions. It will also be understood that each block or step of the control flow diagram, and combinations of blocks or steps in the control flow diagram, can be implemented by special purpose hardware-based computer systems which perform the specified functions or steps, or combinations of special purpose hardware and computer instructions.

Embodiments of the present invention may have many advantages. For example, the present invention may provide a cost effective technique for determining the probability of response to various tongue-base therapies. In addition, methods of the present invention may be performed efficiently, are non- or minimally invasive, and practical (easily utilized in an average clinician's private office). Embodiments of the present invention may allow direct measurement of the upper airway during the awake or supine REM sleep state, are easy and comfortable for the patient, and reliable. Embodiments of the present invention may also enable rapid measurement of MCSPN volume during both supine (maximally protruded mandibular position) and hypotonic supine (mandible at rest) positions of the mandible, as well as rapid calculation of probability of the success/failure at a defined RDI level. Furthermore, once individual patient-specific variables (RDI, BMI, age, and/or gender) are entered into the processing element by the clinician, and objective airway measurements performed, calculation of the probability of treatment success is then performed by the processing element, and the clinician and patient will then be able to proceed based upon objective information. The stereovideoscope facilitates the collection of objective data that may be readily used to provide more accurate and reliable measurements associated with a portion of the patient's anatomy.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for acquiring measurements of a patient's upper airway comprising:
   a stereovideoscope comprising a scope coupled to a flexible tubing and configured to be positioned within the patient's upper airway, said scope comprising a plurality of stereoscopic lenses configured to capture data indicative of a portion of the patient's upper airway, said flexible tubing comprising a biocompatible material; and
   a processing element in communication with said stereovideoscope and configured to generate an image indicative of a portion of the patient's upper airway based on the captured data in order to acquire at least one geometrical measurement indicative of the portion of the patient's upper airway and to determine a probability of the patient's response to a tongue-base treatment based on the at least one geometrical measurement.

2. The system of claim 1, wherein said flexible tubing has a diameter of less than 5 mm.

3. The system of claim 1, wherein said processing element is portable.

4. The system of claim 1, wherein said processing element is configured to generate images in order to acquire at least one measurement selected from a group consisting of linear, angular, depth, profile, and area measurements of the portion of the patient's upper airway.

5. The system of claim 1, wherein said processing element is configured to determine a probability of the patient's response to a tongue-base treatment based on at least one measurement of a most critical site of proximal narrowing of the patient's upper airway with the patient's mandible at rest and the mandible in an advanced position.

6. The system of claim 1, wherein said stereovideoscope comprises a CCD camera.

7. The system of claim 1, wherein said scope is permanently or interchangeably attached to a distal end of said flexible tubing.

8. The system of claim 1, wherein said stereovideoscope is capable of being sterilized.

9. The system of claim 1, wherein said processing element comprises a computer or a monitor.

10. The system of claim 1, wherein said processing element is configured to determine a probability of the patient's response to a tongue-base treatment based on at least an anterior/posterior measurement and a lateral measurement of the portion of the patient's upper airway.

11. The system of claim 10, wherein the anterior/posterior measurement comprises a measurement between the patient's posterior pharyngeal wall and epiglottis tip.

12. The system of claim 10, wherein the lateral measurement comprises a lateral measurement between the pharyngeal wall that is substantially transverse to the anterior-posterior measurement.

13. The system of claim 1, wherein said processing element is configured to determine a probability of the patient's response to a tongue-base treatment based on the at least one acquired geometrical measurement and patient-specific physiological data.

14. The system of claim 13, wherein said processing element is configured to determine a probability of the patient's response to a tongue-base treatment by comparing the at least one acquired geometrical measurement and the patient-specific physiological data to an expected relationship between similar geometrical measurements and patient-specific physiological data obtained from a plurality of other patients.

15. The system of claim 13, wherein the patient-specific physiological data comprises at least one of body mass index, respiratory disturbance index or apnea hypopnea index, age, neck circumference, or gender.

16. The system of claim 1, wherein the processing element is configured to generate a plurality of images of an axial view of a patient's upper airway in a retroepiglottic region, and wherein the processing element is further configured to determine a probability of the patient's response to a tongue-base treatment based on an anterior/posterior measurement and a lateral measurement acquired from the images.

17. The system of claim 16, wherein each image depicts a cross-sectional plane of the patient's upper airway, the cross-sectional plane extending substantially transverse to a longitudinal axis of the patient's pharynx.

18. The system of claim 1, wherein the at least one geometrical measurement comprises an area of a most critical site of proximal narrowing of the upper airway.

19. The system of claim 18, wherein the processing element is configured to determine a percentage area expansion based on the area of the most critical site of proximal narrowing of the upper airway.

* * * * *

UNITED STATES PATENT AND TRADEMARK OFFICE
CERTIFICATE OF CORRECTION

| | | |
|---|---|---|
| PATENT NO. | : 8,162,820 B2 | Page 1 of 1 |
| APPLICATION NO. | : 12/300923 | |
| DATED | : April 24, 2012 | |
| INVENTOR(S) | : Moore | |

It is certified that error appears in the above-identified patent and that said Letters Patent is hereby corrected as shown below:

Column 4,
Lines 9 and 10, "all-corners" should read --all-comers--.

Signed and Sealed this
Twenty-second Day of January, 2013

David J. Kappos
*Director of the United States Patent and Trademark Office*